(12) United States Patent
Singh (10) Patent No.: US 9,554,720 B2
(45) Date of Patent: Jan. 31, 2017

(54) DETECTION OF R-PEAK POINT IN AN ELECTROCARDIOGRAM SIGNAL

(71) Applicant: Gurkirt Singh, Bangalore (IN)

(72) Inventor: Gurkirt Singh, Bangalore (IN)

(73) Assignee: Siemens Medical Solutions USA, Inc., Malvern, PA (US)

( * ) Notice: Subject to any disclaimer, the term of this patent is extended or adjusted under 35 U.S.C. 154(b) by 2 days.

(21) Appl. No.: 14/613,180

(22) Filed: Feb. 3, 2015

(65) Prior Publication Data

US 2016/0220140 A1    Aug. 4, 2016

(51) Int. Cl.
*A61B 5/0456* (2006.01)
*A61B 5/044* (2006.01)

(52) U.S. Cl.
CPC .............. *A61B 5/0456* (2013.01); *A61B 5/044* (2013.01)

(58) Field of Classification Search
CPC .............................. A61B 5/0456; A61B 5/044
See application file for complete search history.

(56) References Cited

U.S. PATENT DOCUMENTS

2006/0015033 A1\* 1/2006 Blakley ................ A61B 5/0424 600/509

OTHER PUBLICATIONS

QRS Complex Detection of ECG Signal by Using Teager Energy Operator, 2008, CN, May 16, 2008.

\* cited by examiner

*Primary Examiner* — Joseph Dietrich
(74) *Attorney, Agent, or Firm* — Lempia Summerfield Katz LLC (57) ABSTRACT

Detection of R-peak signal in an electrocardiogram signal is provided. An electrocardiogram signal representing heart activity of an individual is received. The electrocardiogram signal is sampled to obtain a plurality of sample points, and a bounded non-linear response value is computed for each sample point of the received signal by calculating a negative exponential of derivatives of the sample points.

13 Claims, 11 Drawing Sheets

DETECTION OF R-PEAK POINT IN AN ELECTROCARDIOGRAM SIGNAL

FIELD OF TECHNOLOGY

The present embodiments relate to the field of detection of an electrocardiogram signal.

BACKGROUND

The electrocardiogram (ECG) is a representation of electrical activity of the heart. An ECG signal may be represented by multiple key points of clinical relevance such as QRS, P wave and T wave. The QRS-complex is considered to be the most important waveform in an ECG signal. The QRS-complex includes three characteristic points within one cardiac cycle denoted as Q, R and S. R-peak in such QRS complex is one of the most pivotal points to analyze an ECG signal. Therefore, detection of the QRS-complex is fundamental to the analysis of an ECG signal. Although detection of the QRS-complex is not a problem, noise, pathological signals and variations in amplitudes may result in significantly reduced accuracy and faulty detection of the QRS-complex.

Currently, R-peak in an ECG signal may be detected by several methods. These methods make use of derivative feature responses. Such derivative features are computed and compared against the pre-defined threshold after non-linear filtering to accomplish R-peak detection. For example, in one of the methods for detection of the QRS-complex, the Teager Energy Operator (TEO) is employed to detect characteristic points of the ECG signal. TEO reflects the instantaneous frequency and instantaneous amplitude changes in the signal. The TEO is employed to restrain the P wave, the T-wave, the powerline interference and the baseline wander in an ECG signal. The energy operator uses data obtained from three adjacent sample points. The output of the TEO is proportional to the product of the amplitude and the frequency of the input signal.

However, the method of detection of R-peak point using the TEO has several disadvantages. The method obtains close to 99% QRS complex detection rate on MIT/BIH arrhythmia database. Contrarily, this method fails to provide accurate results where variations in the ECG signal are more than MIT/BIH dataset. Several detections of R-peak points have been faulty, and many R-peak points have been missed. The TEO response in such cases is not very distinctive for T-peak and R-peak. Setting a single threshold for the computed responses is difficult due to the instability.

SUMMARY AND DESCRIPTION

The scope of the present invention is defined solely by the appended claims and is not affected to any degree by the statements within this summary.

The present embodiments may obviate one or more of the drawbacks or limitations in the related art. For example, detection of an R-peak point in an electrocardiogram signal that provides more accurate results in case of real world signals is provided. A bounded non-linear response value for each sample point is computed by taking a negative exponential of derivatives.

One or more of the present embodiments provide a method of detection of an R-peak point in an electrocardiogram signal. According to one or more of the present embodiments, the method includes receiving the electrocardiogram signal. The electrocardiogram signal represents the heart activity of an individual. The electrical activity of the heart is interpreted over a period of time by electrodes that are attached to the surface of the skin of the individual. The electrocardiogram signal recorded includes ECG beats. The method also includes sampling the received electrocardiogram signal so as to obtain a plurality of sample points. The sample points are provided for further analysis of the received electrocardiogram signal. The method further includes computing a bounded non-linear response value for each sample point of the received signal. The amplitudes of the sample points of the received signal are chosen, and a non-linear response is computed.

According to one or more of the present embodiments, the bounded non-linear response value for each sample point is computed by obtaining a negative exponential of derivatives of neighboring sample points.

The computing of the bounded non-linear response value for each sample point includes identifying a reference sample point from the plurality of the sample points. The derivatives of the reference sample point are computed in the local neighborhood on both sides of the reference sample point. This helps in capturing a sharp change in the received electrocardiogram signal. If the change in the neighborhood is high, the value obtained for the derivatives is high. The computing of the probabilistic non-linear response value further includes calculation of a negative exponential of the derivatives. An absolute derivative of a given sample point may be misleading due to factors like baseline shifts, noise and ST elevation. In order to get a response value that is invariant to the factors, a negative exponential of the derivatives is calculated. Therefore, the negative exponential helps in creating a notion of a probabilistic response that is bounded between 0 and 1. A product of the computed response values generates a consensus for the R-peak point.

According to one or more of the present embodiments, detection of an R-peak point in the received signal includes applying a threshold to the computed bounded non-linear response values and determining maxima of the received signal based on the threshold. The maxima represent the R-peak point of the received electrocardiogram signal. Application of threshold distinguishes the R-peak point from other peaks generated in the signal. The threshold is applied on a trial and error basis. The maximum response value generated is monitored, and the threshold is set. Therefore, the response values that cross the threshold depict the R-peak points in the received electrocardiogram signal.

According to one or more of the present embodiments, the maxima of the signal are obtained where the response value after applying the threshold is 1. Therefore, determination of the R-peak points on the signal is easier.

According to one or more of the present embodiments, the bounded response value lies between 0 and 1. The negative exponential of the derivatives of the sample points generates a response value that always lies between 0 and 1.

According to one or more of the present embodiments, the sample points on the received signal are identified by choosing points on the received signal at regular intervals of time. Therefore, the sample points are spaced out evenly on the received signal.

A device for processing electrocardiogram signals is also provided.

A device for processing electrocardiogram signals such that an R-peak point in the signal is detected is provided. According to one or more of the present embodiments, the device includes a communication interface. The communication interface is configured to receive electrocardiogram signals of an individual. The communication interface receives the heart activity of the individual by electrodes connected to the body of the individual. These electrodes transmit the electrical activity of the heart of the individual, which is received and recognized by the communication interface.

According to one or more of the present embodiments, the device further includes a module to detect an R-peak point in the received electrocardiogram signal. The module is configured to identify sample points on the received signal. The sample points are chosen on the received signal such that the sample points are spaced evenly based on regular intervals of time. The module is further configured to compute a probabilistic non-linear response value for each reference sample point on the received signal and detect an R-peak point in the electrocardiogram signal.

According to one or more of the present embodiments, in order to compute a bounded non-linear response, the R-peak detection module is configured to compute derivatives of the sample points on the received signal. The derivatives are calculated on both sides of the sample point so that a sharp change in the received signal may be detected. Once the derivatives are computed, a negative exponential of the derivatives is calculated by the R-peak detection module. An absolute derivative of a given sample point may be misleading due to factors like baseline shifts, noise and ST elevation. In order to get a response value that is invariant to the factors, a negative exponential of the derivatives is calculated. Therefore, the negative exponential helps in creating a notion of a probabilistic response.

According to one or more of the present embodiments, the device is further configured to apply a threshold to the computed bounded non-linear response values and detect a maxima of the non-linear response values in a given set of response values based on the threshold. Application of threshold is important so as to distinguish the R-peak point from other peaks generated in the signal. The maximum response value generated is monitored, and the threshold is set. Therefore, the response values that cross the threshold depict the R-peak points in the received electrocardiogram signal.

According to one or more of the present embodiments, the maximum of the signal is obtained where the response after applying the threshold is 1. Therefore, determination of the R-peak points on the signal is easier.

According to one or more of the present embodiments, the R-peak detection module is configured to choose points on the received signal at regular intervals of time. Therefore, the sample points are spaced out evenly on the received signal.

According to one or more of the present embodiments, the device includes a display module that is configured to display the detected R-peak point.

The present embodiments also relate to a non-transitory computer-readable storage medium having machine-readable instructions stored therein. The machine-readable instructions may be executed by a processor, causing the processor to perform acts. The acts pertain to detection of R-peak point in an electrocardiogram signal. The acts include receiving an electrocardiogram signal from an individual. The electrocardiogram signal represents the heart activity of the individual and includes ECG beats. Further, the method includes sampling the received electrocardiogram signal such that a plurality of sample points is obtained. The sample points are obtained at regular intervals of time. The method also includes computing a probabilistic non-linear response for each sample point of the received signal. The probabilistic non-linear response value depicts the R-peak point of the received electrocardiogram signal.

According to one or more of the present embodiments, the storage medium further includes instructions that cause the processor to perform acts of identifying a reference sample point from the plurality of sample points on the electrocardiogram signal. The derivatives of the sample point are computed in the local neighborhood on both sides of the reference sample point. This helps in the detection of a sharp change in the received signal. The acts further include calculating a negative exponential of the derivatives. Therefore, a probabilistic non-linear response value of the reference sample points may be computed.

According to one or more of the present embodiments, the storage medium further includes instructions that cause the processor to apply a threshold to the computed probabilistic non-linear response values and determine maxima of the non-linear response value in a given set of non-linear response values based on the threshold. Application of threshold is provided so as to distinguish the R-peak point from other peaks generated in the signal. The maximum response value generated is monitored, and the threshold is set. Therefore, the response values that cross the threshold depict the R-peak points in the received electrocardiogram signal.

DETAILED DESCRIPTION

The various embodiments are described with reference to the drawings, where like reference numerals are used to refer to like elements throughout. In the following description, for purpose of explanation, numerous specific details are set forth in order to provide a thorough understanding of one or more embodiments. Such embodiments may be practiced without these specific details.

Figure 1:
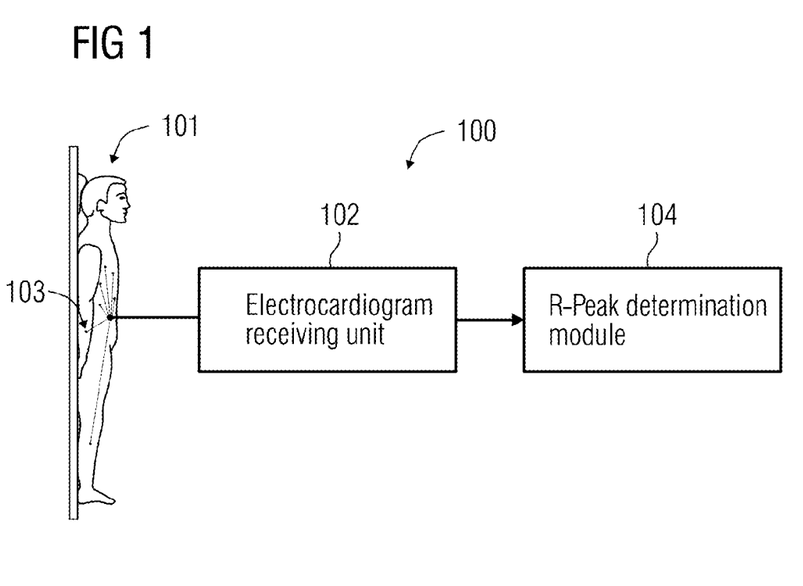
FIG. 1 illustrates a block diagram of an embodiment of an electrocardiogram monitoring environment.

FIG. 1 shows a block diagram of one embodiment of an electrocardiogram monitoring environment 100. In the environment 100, an electrocardiogram signal of an individual 101 is recorded and is monitored. The electrocardiogram signal depicts the electrical activity of the heart. The electrical activity is measured over a period of time to compute electrocardiogram signals. A typical electrocardiogram signal includes a P wave, a QRS complex, a T wave and a U wave. These waveforms are generated as a result of polarization and depolarization of cardiac tissues. The waveform is then used to measure the rate and regularity of the heartbeats of the individual 101. The QRS complex in the electrocardiogram is of higher clinical relevance. The R-peak in a QRS complex in an electrocardiogram signal is analyzed the most for heart related ailments. The continuous detection of R-peak provides an easy method of computing the heart rate of an individual.

Figure 2:
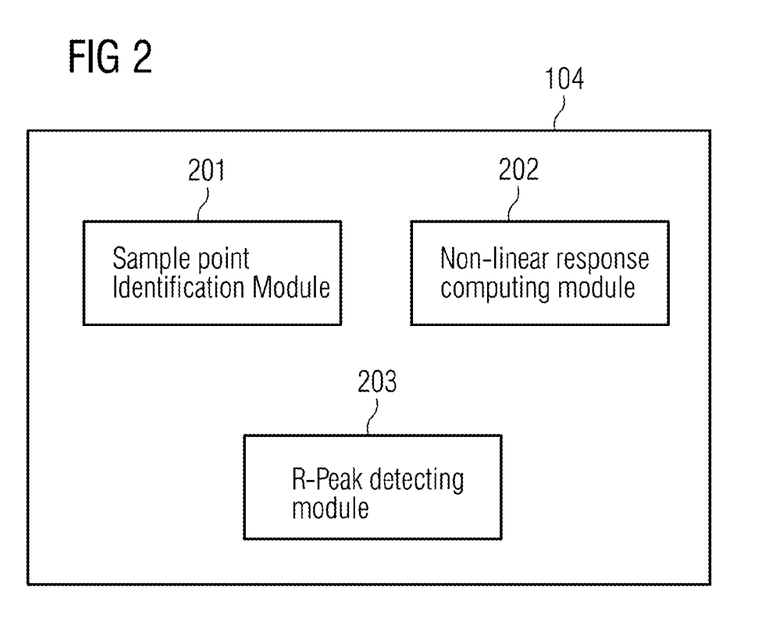
FIG. 2 illustrates a block diagram of an embodiment of a module for determination of R-peak in a received electrocardiogram signal.

The health monitoring environment 100 includes an electrocardiogram receiving unit 102 that receives the electrocardiogram signal from the individual 101. The individual 101 has electrodes 103 attached to the surface of his skin. The electrocardiogram signal is then received and recorded by the electrocardiogram receiving unit 102. The health monitoring environment 100 further includes an R-peak determination module 104 that helps in recognition of the R-peak in an electrocardiogram signal. In a condition of a change in the behavior of the heart, detection of R-peak in a QRS complex becomes difficult. The R-peak determination module 104 makes use of an R-peak detection module for accurate detection of the R-peak in the electrocardiogram signal FIG. 2 shows a block diagram of an embodiment of an R-peak determination module 104. The R-peak determination module 104 includes a sample point identification module 201. The sample point identification module 201 identifies sample points on the received electrocardiogram signal based on a specific time interval.

Therefore, each sample point on the electrocardiogram signal is spaced out equally. R-peak point in an electrocardiogram signal is a point of high change in the amplitude of the electrocardiogram signal. Therefore, sampling the electrocardiogram signal helps in determination of the point at which the change in the amplitude is very high. The sample point identification module makes use of algorithms known to a person skilled in the art and may be device specific. The R-peak determination module 104 further includes a nonlinear response computing module 202. Once the sample points are identified on the electrocardiogram signal, a reference sample point is chosen. For the reference sample point, a derivative is computed in the local neighborhood on both sides. A local neighborhood is an area of a defined window size surrounding the reference sample point. If the change in the neighborhood is high, then the value of the derivatives obtained is high. However, such an absolute derivative response may be misleading due to several variations in the electrocardiogram signal caused due to factors like, for example, baseline shift, noise and ST elevation. In order to obtain a response that is invariant to the factors, a negative exponential of the derivatives is computed. Therefore, the negative exponential of the derivatives gives indicates a probabilistic response. The product of these responses generates a consensus for R-peak in the received electrocardiogram signal. The response is computed for the received signal with a set of N sample points using the following algorithm:

$$R[n] = 1 + \pi_{k=-K}^{K} e^{-(x[n]-x[n-k])^2/s}$$

where R is response, K is neighborhood window size, X is amplitude of the received electrocardiogram signal, and s is a scale computed from the signal. The scale s is a factor by which difference in derivatives is divided to get a desired response value.

$$s = 4 * \max(|x[n] - x[n+2]|)$$

where n varies from 1 to L and where L is the length of considered signal for computing the scale factor.

The bounded response derived from the algorithm always lies between 0 and 1. Therefore, post processing steps, if any, are easier. The R-peak determination module also includes an R-peak detecting module 203. The module 203 helps in application of a threshold to the computed set of response values of the sample points so as to find the maximum amplitude point on the signal. The response value after application of threshold is to be 1. Instead of applying a single threshold, an adaptive thresholding technique may also be applicable to obtain the maximum amplitude point on the electrocardiogram signal. Such method of adaptive thresholding may be useful when the variation in the electrocardiogram signal is very high.

Figure 3:
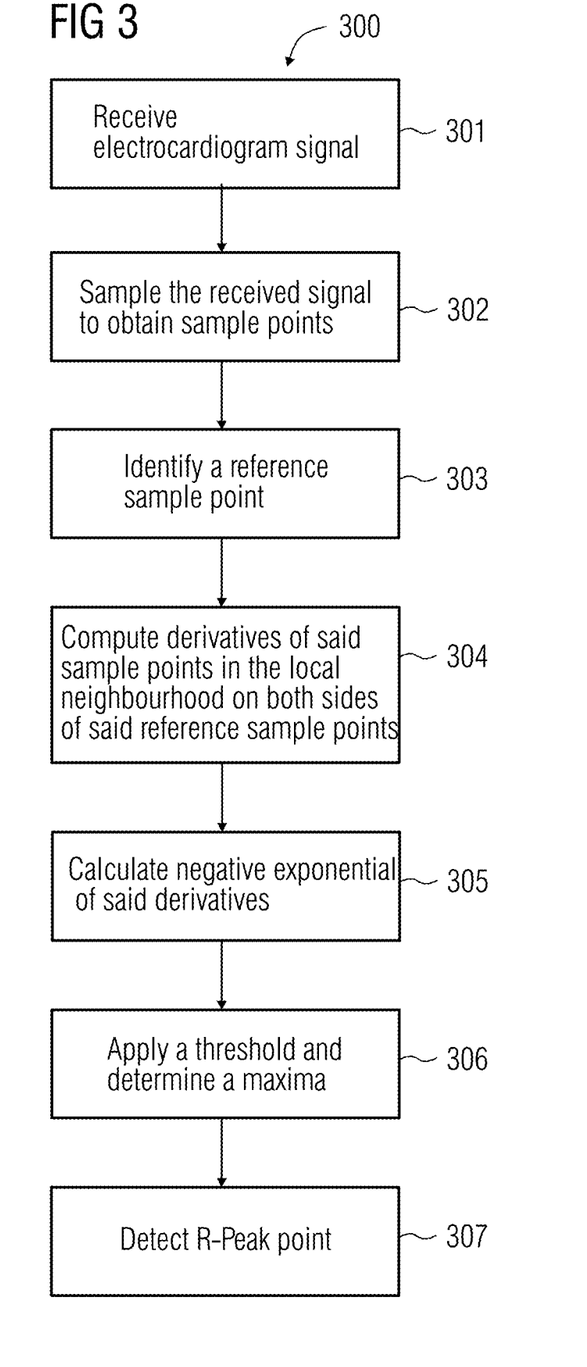
FIG. 3 illustrates a schematic diagram of a flowchart of an embodiment of a method of detection of R-peak point in the received electrocardiogram signal.

FIG. 3 shows a flowchart of an embodiment of a method 300 for detection of an R-peak point in an electrocardiogram signal. In act 301 of the method, an electrocardiogram signal is received from an individual 101. Electrodes 103 are attached to the skin surface of the individual 101, and the electrical activity of the heart of the individual 101 is received and recorded by the electrocardiogram receiving unit 102. Once the electrocardiogram signal is received, in act 302, the signal is sampled to obtain sample points. In act 303, a reference sample point is chosen from the set of sample points. Subsequently, in act 304, derivatives of the reference sample points are computed in the local neighborhood on both sides of the reference sample points. If the change in amplitude of the electrocardiogram signal in the local neighborhood is high, the value of the derivative is higher. A sudden change in the amplitude of the electrocardiogram signal helps in the detection of the R-peak point. However, absolute value of derivatives may not be relied upon due to various actors like baseline shift, noise and ST elevation. In order to avoid these factors, in act 305, a negative exponential of the computed derivatives is calculated. This helps in obtaining a bounded response that always lies between 0 and 1. Further, in act 306, a threshold is applied to the computed responses so as to find the maximum amplitude point on the received signal where the response after application of threshold is 1. Based on the maxima determined, R-peak point is detected in the electrocardiogram signal in act 307.

Figure 4:
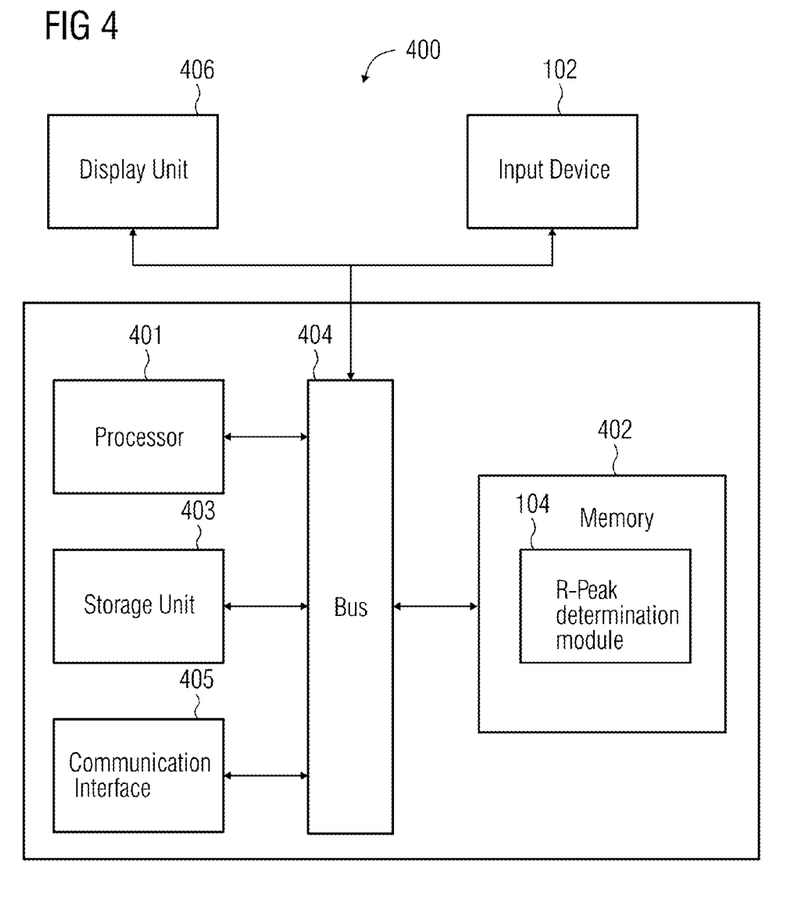
FIG. 4 illustrates a block diagram of an embodiment of a device for detection of an R-peak point in a given electrocardiogram signal.

FIG. 4 illustrates a schematic block diagram of one embodiment of a device 400 for detection of R-peak point in a received electrocardiogram signal. The device 400 includes a processor 401, a memory 402, a storage unit 403, a bus 404, a communication interface 405, a display unit 406 and an input device 102.

Some of the components typical of conventional devices for detection of R-peak point in a received electrocardiogram signal are shown in simplified form or not shown at all in FIG. 4 for purposes of brevity. Such components may nevertheless be provided as part of or for use with the device 400 for detection of R-peak point in a received electrocardiogram signal. Further, such components are well understood in the medical devices art, and therefore, further discussion herein is not necessary for a complete understanding.

The processor 401 may include one or more processors (e.g., a single central-processing unit or a plurality of processing units (a parallel processing environment)). Each of the processors may be any type of computational circuit such as, but not limited to, a microprocessor, a microcontroller, a complex instruction set computing microprocessor, a reduced instruction set computing microprocessor, a very long instruction word microprocessor, an explicitly parallel instruction computing microprocessor, a graphics processor, a digital signal processor, or any other type of processing circuit. The processor 401 may also include embedded controllers, such as generic or programmable logic devices or arrays, application specific integrated circuits, single-chip computers, and the like.

The memory 402 may be volatile memory and non-volatile memory. A variety of computer-readable storage media may be stored in and accessed from the memory 402. The memory 402 may include any suitable elements for storing data and machine-readable instructions, such as read only memory, random access memory, erasable programmable read only memory, electrically erasable programmable read only memory, hard drive, removable media drive for handling compact disks, digital video disks, diskettes, magnetic tape cartridges, memory cards, and the like. The memory 402 includes an R-peak determination module 104. The module 104 may be stored in the form of machine-readable instructions on any of the above mentioned storage media and may be executed by the processor 401.

The communication interface 405 receives the ECG signal representing the electrical activity of the heart of the individual from the electrodes 103 of FIG. 1. The display unit 406 displays the response computed detecting the R-peak point on the ECG signal. The bus 404 acts as interconnect between various components of the dedicated device 400 for detection of R-peak in an electrocardiogram signal. The input device 102 is well known to one of ordinary skill in the art, and hence, the explanation is thereof omitted.

FIG. 5A-H illustrate graphical representations of various embodiments of responses 502 obtained for different types of electrocardiogram signals 501. The X-axis of the graph represents the time in seconds (s), while the Y axis depicts amplitude of the signal in millivolts (mV). The electrocardiogram signals 501 are depicted by waves recorded on the bottom half of the graph, while the responses 502 computed and recorded for the electrocardiogram signals 501 are depicted on the upper half of the graph.

Figure 5A:
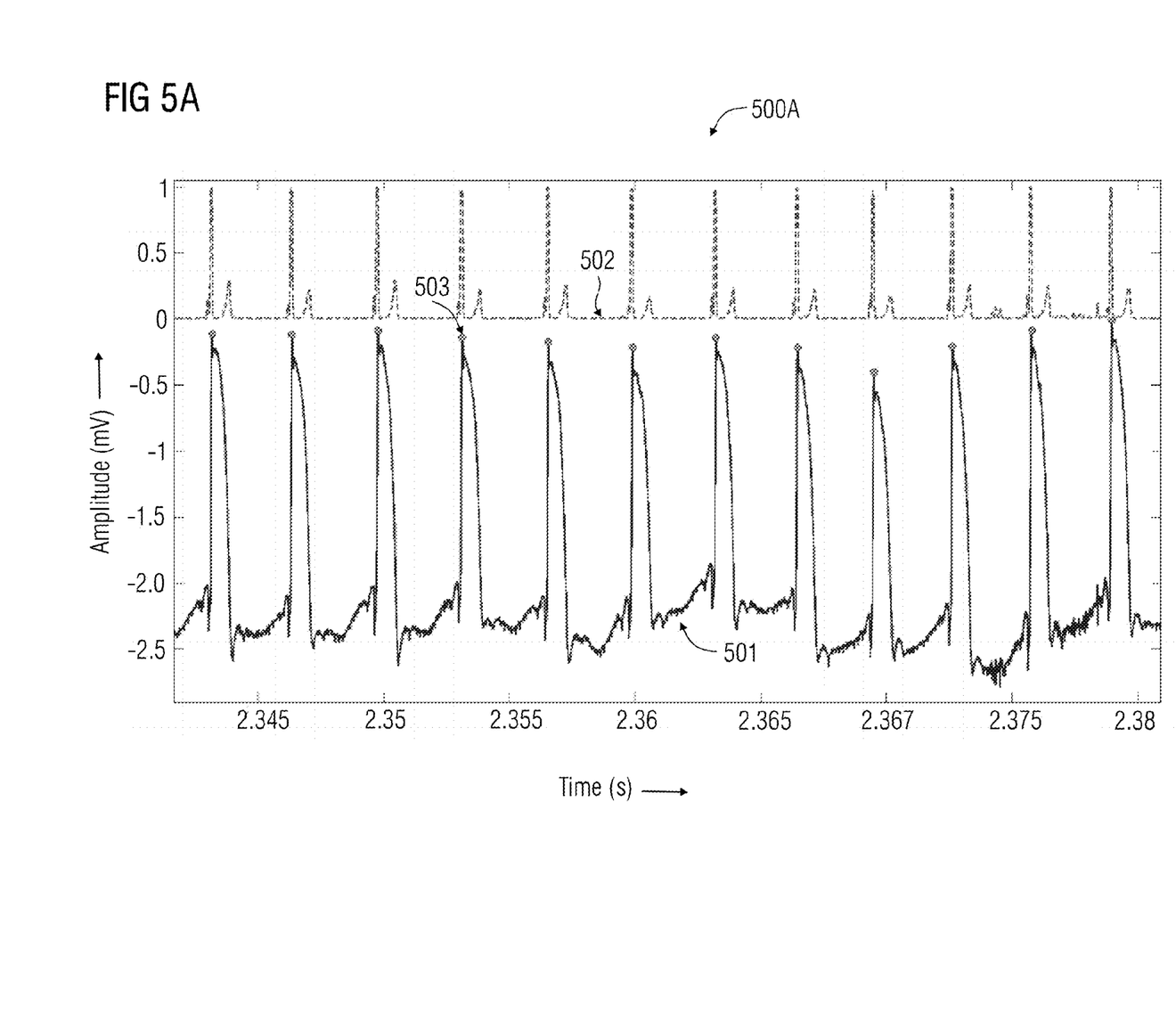
FIG. 5A illustrates a graph of an embodiment of a response obtained for an abnormal electrocardiogram signal.

FIG. 5A illustrates a graphical representation 500A of an embodiment of a response 502 obtained for an electrocardiogram signal 501 that has severe abnormality. The electrocardiogram signal 501 represented in the graph has deviations in comparison to a normal electrocardiogram signal. The signal 501 also suffers from noise. However, the response 502 obtained for R-peak 503 is seen to be accurate. The response 502 for R-peak 503 occurs exactly at the point where the amplitude of the signal 501 is the highest. Therefore, detection of R-peak 503 in case of abnormality in signal is easier and precise.

Figure 5B:
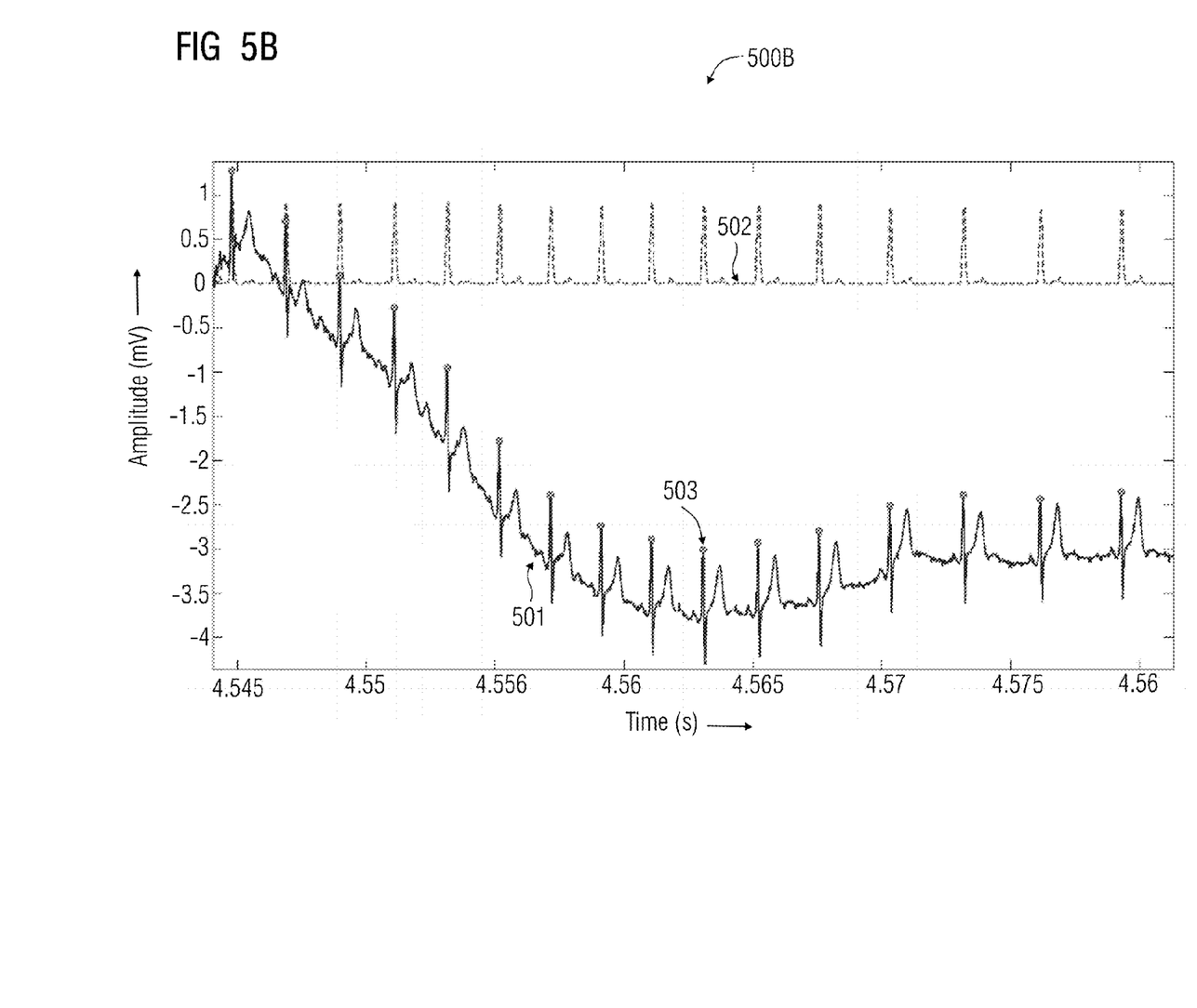
FIG. 5B illustrates a graph of an embodiment of a response obtained for an electrocardiogram signal with high baseline shift.

FIG. 5B provides a graphical representation 500B of an embodiment of a response 502 computed for an electrocardiogram signal 501 with high baseline shift. The baseline of an electrocardiogram signal is measured as the portion of the tracing following the T wave and preceding the next P wave, and the segment between the P wave and the following QRS complex. In a normal healthy heart, the baseline is equivalent to the isoelectric line (0 mV) and represents the periods in the cardiac cycle when there are no currents towards either the positive or negative ends of the ECG leads. However, the baseline may be depressed or elevated in a diseased heart. The graph represents the response 502 computed for the electrocardiogram signal 501 that suffers from a baseline shift. The locations of the R-peaks 503 detected are accurate, and there are no missed detections or false detections observed.

Figure 5C:
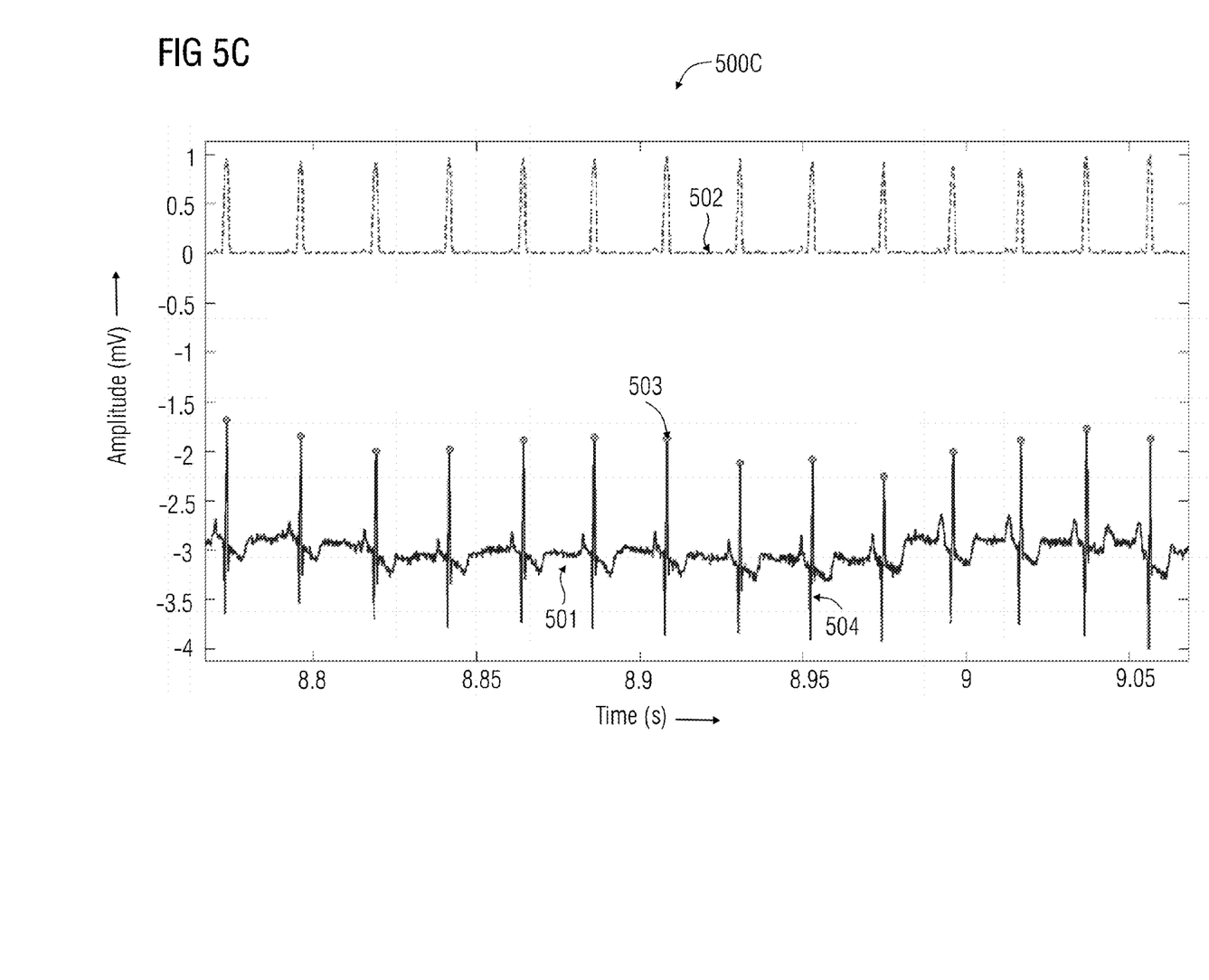
FIG. 5C illustrates a graph of an embodiment of a response obtained for an electrocardiogram signal with depression and noise.

FIG. 5C illustrates a graph 500C of an embodiment of a response 502 obtained for an electrocardiogram signal 501 suffering from depression and noise. In the electrocardiogram signal 501 depicted in the graph, the ST segment 504 in the signal is significantly depressed. The signal 501 also has noise, making the detection of R-peak 503 difficult. However, the response 502 computed is free of errors and is located exactly where the amplitude of the signal 501 is recorded as highest.

Figure 5D:
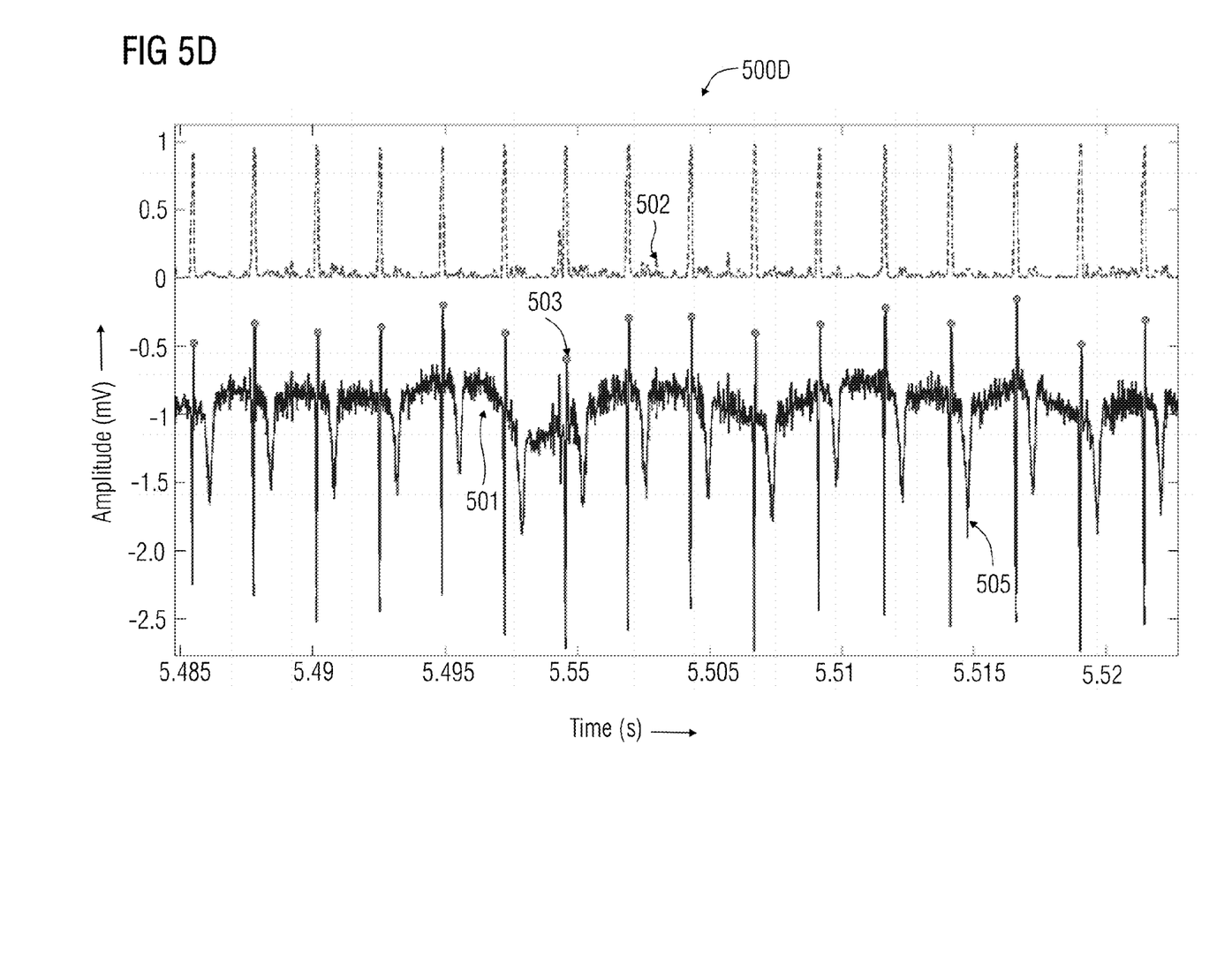
FIG. 5D illustrates a graph of an embodiment of a response obtained for an electrocardiogram signal with depression and more noise.

FIG. 5D illustrates a graph 500D of another embodiment of a response 502 computed for an electrocardiogram signal 501 suffering from noise and inverted T-peak 505. The noise recorded in the electrocardiogram signal 501 is considerably high in comparison with that of a normal one. The inversion in T-peak 505 observed in the signal 501 also is quite high. The response 502 is computed for the R-peak point 503 on the electrocardiogram signal 501 without any pre-conditioning. The response 502 computed is unambiguous and accurate.

Figure 5E:
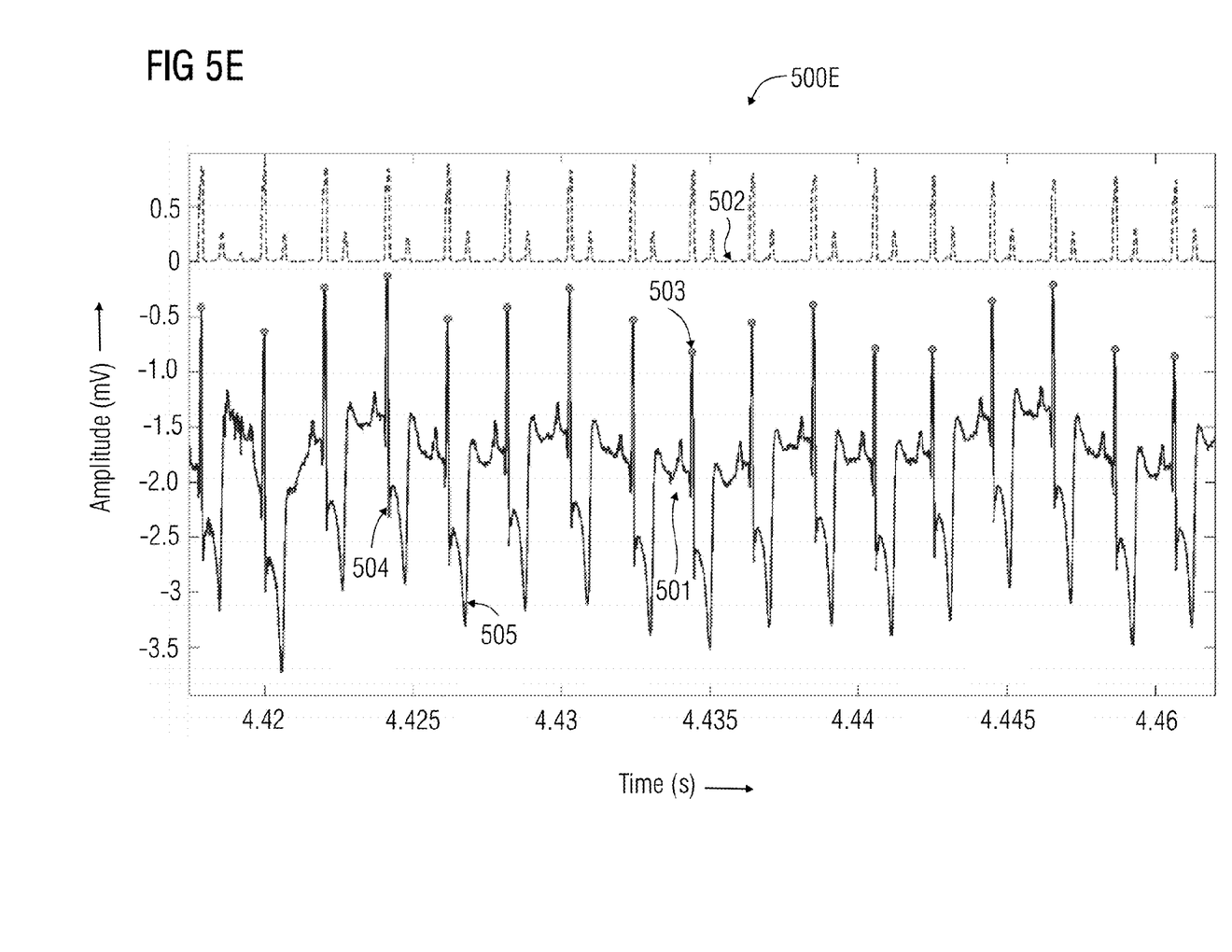
FIG. 5E illustrates a graph of an embodiment of a response obtained for an electrocardiogram signal where the T-peak is inverted.

FIG. 5E illustrates a graph 500E of an embodiment of a response 502 computed for an electrocardiogram signal 501 with ST depression 504 and inverted T peak 505 and noise. In a diseased condition, certain electrocardiogram signals may show the presence of inverted T-peaks 505 along with some noise. The disclosure helps in computing an accurate response 502 for R-peaks in such electrocardiogram signals 501. The responses 502 point out accurately to the R-peaks 503 in the abnormal electrocardiogram signal 501. This enhances the reliability of the disclosure.

Figure 5F:
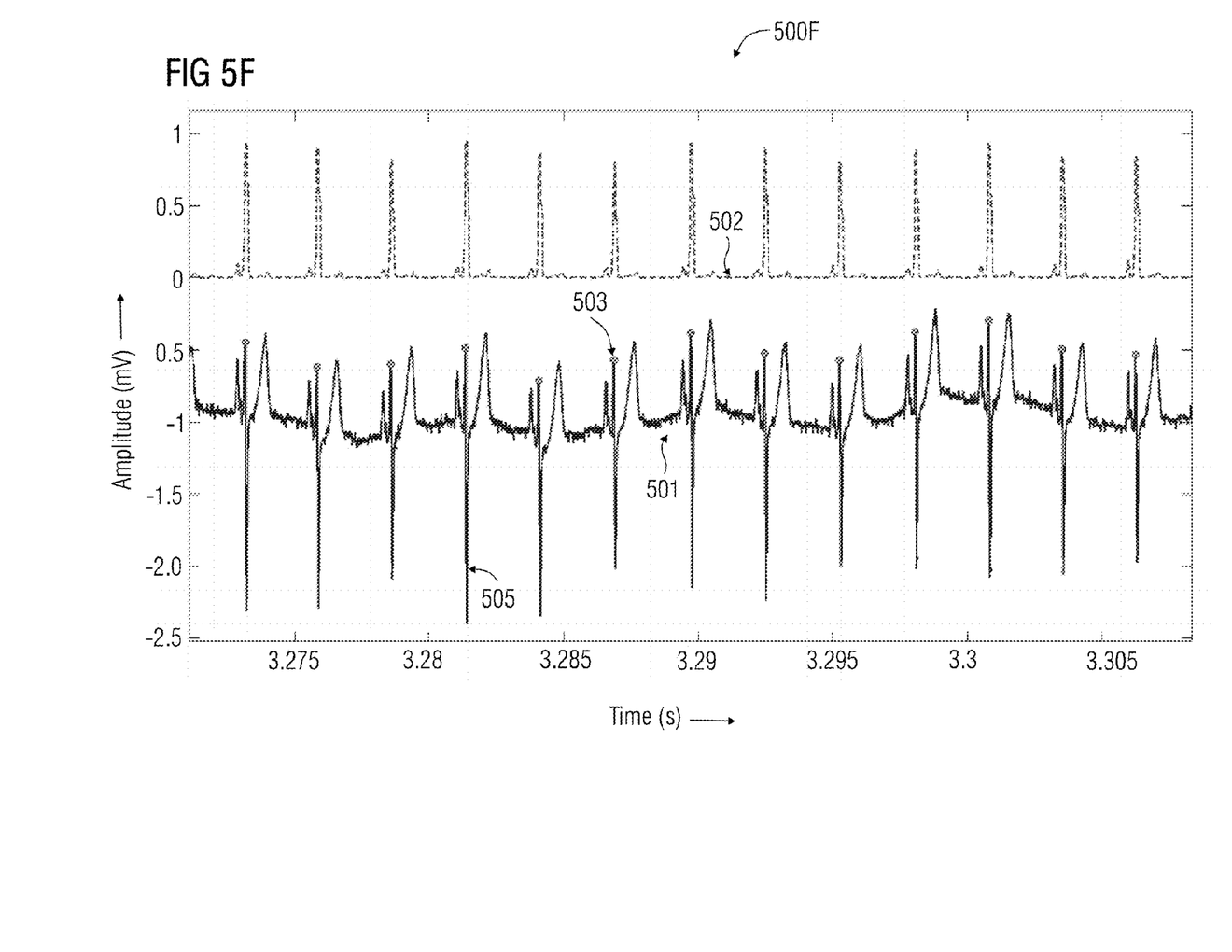
FIG. 5F illustrates a graph of an embodiment of a response obtained for an electrocardiogram signal where T-peak is higher than R-peak.

FIG. 5F provides a graphical representation 500F of an embodiment of a response 502 recorded for an electrocardiogram signal 501, where T-peak 505 in the signal is higher than the R-peak 503. The disclosure also responds well to a diseased condition of the heart where the T-peak 505 is higher than the R-peak 503 in the signal. The disclosure computes responses 501 for R-peaks 503 based on the sudden changes in the amplitude of the electrocardiogram signal 501. In this case, the first sudden elevation in the amplitude of the signal 501 is taken into consideration to determine the R-peak point 503.

Figure 5G:
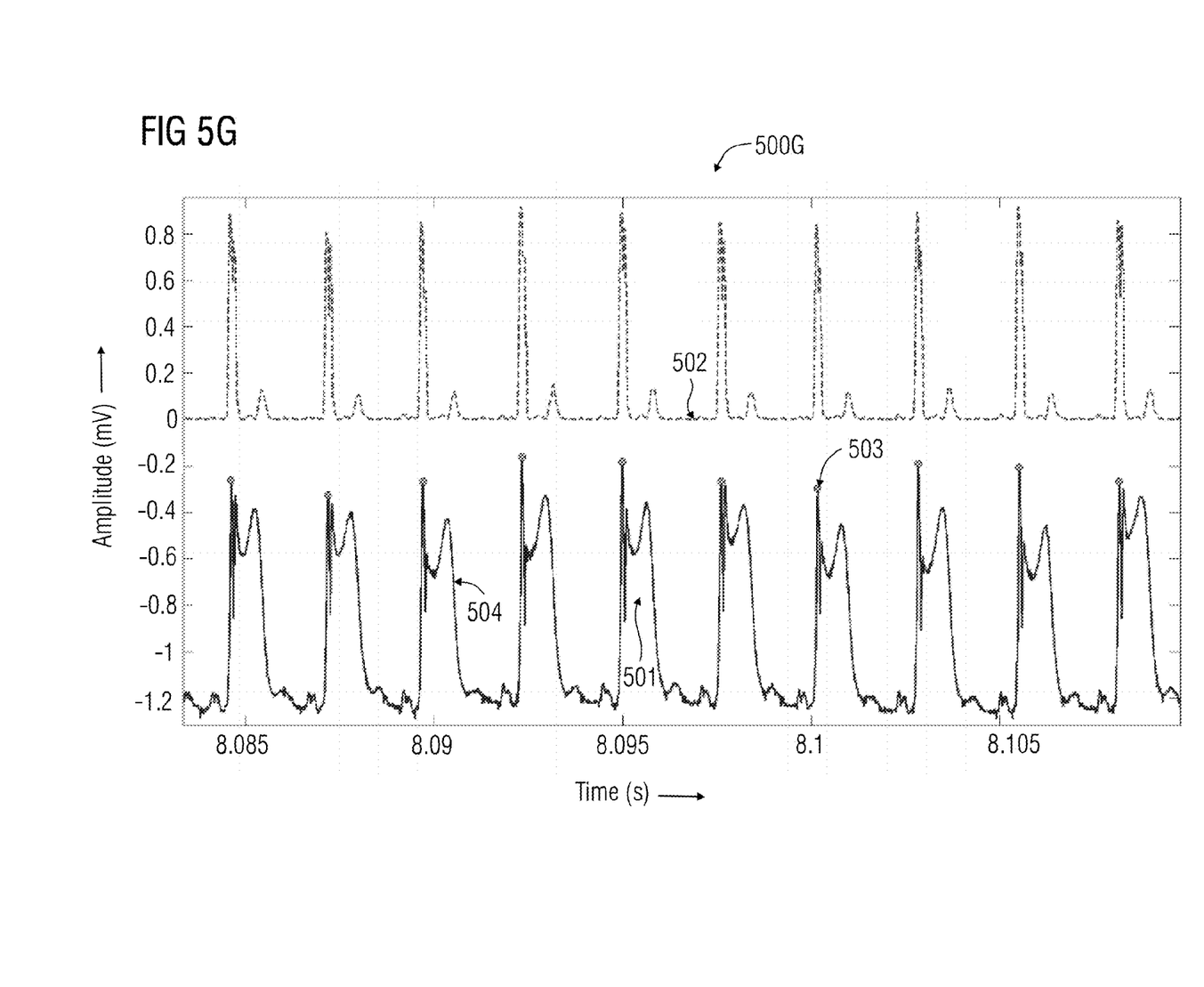
FIG. 5G illustrates a graph of an embodiment of a response obtained for an electrocardiogram signal with elevated ST segment.

FIG. 5G provides a graphical representation 500G of an embodiment of a response 502 recorded for an electrocardiogram signal 501, where the ST segment 504 is elevated. In a normal condition, ST segment 504 of an electrocardiogram signal 501 is small and does not show high elevation. In a diseased condition, where the electrocardiogram signal 501 of an individual shows elevation of the ST segment 504, detection of R-peak 503 may be difficult. One or more of the present embodiments work well in such conditions by computing a correct response 502. The response value recorded for R-peak point 503 of the electrocardiogram signal 501 is highest, and therefore, determination of the peak point 503 is easier.

Figure 5H:
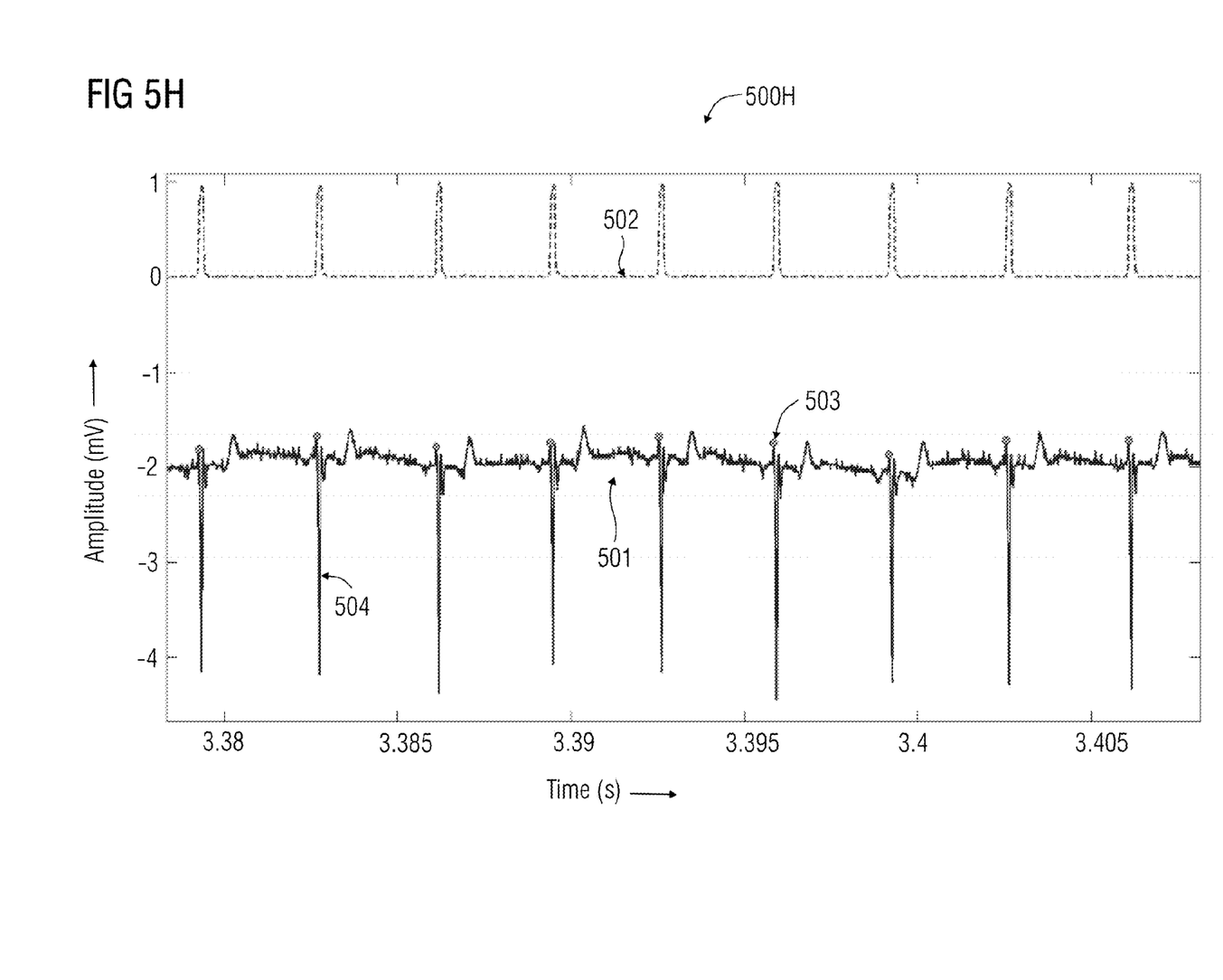
FIG. 5H illustrates a graph of an embodiment of a response obtained for an electrocardiogram signal with depressed ST segment and low R-peak amplitude.

FIG. 5H illustrates a graph 500H of an embodiment of a response 502 recorded for an electrocardiogram signal 501, where the ST segment 504 is depressed, and the amplitude of R-peak point 503 is low. One or more of the present embodiments have been successful in recording accurate responses for R-peak points 503 in such diseased conditions. The responses 502 are recorded at exact locations of R-peak 503 points on the received signal 501.

One or more of the present embodiments may take the form of a computer program product including program modules accessible from computer-usable or computer-readable medium storing program code for use by or in connection with one or more computers, processors, or instruction execution system. For the purpose of this description, a computer-usable or computer-readable medium may be any apparatus that may contain, store, communicate, propagate, or transport the program for use by or in connection with the instruction execution system, apparatus, or device. The medium may be an electronic, magnetic, optical, electromagnetic, infrared, or semiconductor system (or apparatus or device), or propagation mediums as signal carriers that are not included in the definition of physical computer-readable medium. The medium may include a semiconductor or solid state memory, magnetic tape, a removable computer diskette, random access memory (RAM), a read only memory (ROM), a rigid magnetic disk and optical disk such as compact disk read-only memory (CD-ROM), compact disk read/write, and DVD. Both processors and program code for implementing each aspect of the technology may be centralized or distributed (or a combination thereof) as known to those skilled in the art.

While the present invention has been described in detail with reference to certain embodiments, the present invention is not limited to these embodiments. In view of the present embodiments, many modifications and variations may be provided by those skilled in the art without departing from the scope of the invention. The scope of the present invention is therefore indicated by the following claims rather than by the foregoing description. All changes, modifications, and variations coming within the meaning and range of equivalency of the claims are to be considered within their scope.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method of detection of R-peak point in an electrocardiogram signal, the method comprising:
   receiving, by a processor from an electrocardiogram (ECG) device for processing ECG signals, an ECG signal representing heart activity of an individual, wherein the ECG signal comprises ECG beats;
   obtaining, by the processor, a plurality of sample points, the obtaining comprising sampling the received ECG signal;
   computing, by the processor, a bounded nonlinear response value for each sample point of the received ECG signal, the computing comprising taking a negative exponential of derivatives of the plurality of sample points; and
   determining a maxima of the bounded nonlinear response value in a given set of non-linear response values based on a threshold, wherein the maxima represents the R-peak point.

2. The method of claim 1, wherein computing the bounded non-linear response value further comprises:
   identifying a reference sample point from the plurality of sample points;
   computing derivatives of the plurality of sample points in a local neighborhood on both sides of the reference sample point; and
   calculating a negative exponential of the derivatives.

3. The method of claim 1, wherein the maxima of the ECG signal is obtained where the bounded non-linear response value after applying the threshold is 1.

4. The method of claim 3, wherein the bounded non-linear response value lies between 0 and 1.

5. The method of claim 1, wherein obtaining the plurality of sample points on the received ECG signal comprises choosing points on the received ECG signal at regular intervals of time.

6. A device for processing electrocardiogram signals, the device comprising:
   a communication interface configured to receive an electrocardiogram (ECG) signal representing heart activity of an individual, the received ECG signal comprising ECG beats; and
   a processor configured to:
      identify sample points on the received ECG signal;
      compute a bounded non-linear response value for each reference sample point on the received ECG signal; and
      detect an R-peak point in the received ECG signal by determining a maxima of the bounded non-linear response value in a given set of non-linear response values based on a threshold, wherein the maxima represents the R-peak point.

7. The device of claim 6, wherein in the computation of the bounded non-linear response value, the processor is further configured to:
   compute derivatives of the sample points in a local neighborhood on both sides of the reference sample point; and
   calculate a negative exponential of the derivatives.

8. The device of claim 6, wherein the maxima of the received ECG signal is determined when the bounded non-linear response value is 1.

9. The device of claim 6, wherein in the identification of the sample points on the received ECG signal, the processor is configured to choose points on the received ECG signal at regular intervals of time.

10. The device of claim 6, further comprising:
    a display unit configured to display the detected R-peak point.

11. A non-transitory computer-readable storage medium storing machine-readable instructions executable by a processor to process electrocardiogram (ECG) signals, the instructions comprising:

receiving, by the processor, an ECG signal representing heart activity of an individual, the received ECG signal comprising ECG beats;

sampling, by the processor, the received ECG signal to obtain a plurality of sample points; and computing, by the processor, a bounded non-linear response value for each sample point of the received ECG signal.

12. The non-transitory computer-readable storage medium of claim 11, wherein the instructions further comprise:

identifying a reference sample point from the plurality of sample points;

computing derivatives of the plurality of sample points in a local neighborhood on both sides of the reference sample point;

calculating a negative exponential of the derivatives; and computing the bounded non-linear response of the plurality of sample points based on the negative exponential of the derivatives.

13. The non-transitory computer-readable storage medium of claim 11, wherein the instructions further comprise:

applying a threshold to the computed bounded non-linear response values; and determining a maxima of the non-linear response value in a given set of non-linear response values based on the threshold, wherein the maxima represents a R-peak point.

* * * * *